US006336914B1

United States Patent
Gillespie, III

(10) Patent No.: US 6,336,914 B1
(45) Date of Patent: Jan. 8, 2002

(54) RELEASABLE INTERLOCK ASSEMBLY HAVING AXIAL AND ROTATIONAL ENGAGEMENT

(76) Inventor: Richard D. Gillespie, III, 6136 FM 1616, Athens, TX (US) 75751

( * ) Notice: Subject to any disclaimer, the term of this patent is extended or adjusted under 35 U.S.C. 154(b) by 0 days.

(21) Appl. No.: 09/482,838

(22) Filed: Jan. 13, 2000

(51) Int. Cl.[7] .............................................. A61M 5/178
(52) U.S. Cl. .................. 604/165.01; 604/523; 604/533
(58) Field of Search ............................ 604/165.01, 523, 604/533, 534, 535, 538, 539, 164.01, 164.04, 164.07, 165.02–165.04

(56) References Cited

U.S. PATENT DOCUMENTS

| 4,192,305 A | 3/1980 | Seberg ..................... 128/214.4 |
| 4,306,562 A | 12/1981 | Osborne ..................... 128/348 |
| 4,609,370 A | 9/1986 | Morrison ..................... 604/165 |
| 4,682,981 A | 7/1987 | Suzuki et al. ............... 604/158 |
| 4,772,266 A | 9/1988 | Groshong ................... 604/164 |
| 4,946,443 A | 8/1990 | Hauser et al. .............. 604/165 |
| 4,986,814 A | 1/1991 | Burney et al. .............. 604/164 |
| 5,064,414 A | 11/1991 | Revane ........................ 604/165 |
| 5,098,392 A | 3/1992 | Fleischhacker et al. ...... 604/165 |
| 5,098,393 A | 3/1992 | Amplatz et al. ............. 604/167 |
| 5,141,497 A | 8/1992 | Erskine ...................... 604/165 |
| 5,167,634 A | 12/1992 | Corrigan, Jr. et al. ...... 604/160 |
| 5,221,263 A | 6/1993 | Sinko et al. ................. 604/161 |
| 5,250,036 A | 10/1993 | Farivar ....................... 604/164 |
| 5,334,157 A | 8/1994 | Klein et al. ................. 604/160 |
| 5,368,574 A | 11/1994 | Antonacci et al. .......... 604/164 |
| 5,391,152 A | 2/1995 | Patterson ..................... 604/165 |
| 5,403,283 A | 4/1995 | Luther ......................... 604/164 |
| 5,531,701 A | 7/1996 | Luther ......................... 604/165 |
| 5,536,255 A | 7/1996 | Moss ........................... 604/161 |
| 5,741,084 A * | 4/1998 | Del Rio et al. ............. 403/349 |
| 5,772,660 A * | 6/1998 | Young et al. |

* cited by examiner

Primary Examiner—Anhtuan T. Nguyen
Assistant Examiner—Ann Y. Lam
(74) Attorney, Agent, or Firm—John A. Thomas

(57) ABSTRACT

A releasable interlock assembly having axial and rotational engagement, and suitable for use in catheter introducers and other medical devices, has a tapered female member which receives a tapered male member. The female member has protrusions which engage corresponding grooves on the male member. The grooves have a generally axially aligned portion and a generally circumferentially aligned portion, terminating in a pocket to receive the corresponding protrusion on the female member. The depth of the each groove decreases from the open axially aligned end to a point just before the pocket, causing a dimensional interference which prevents the protrusion from disengaging the pocket axially, unless deliberately rotated by an operator.

36 Claims, 9 Drawing Sheets

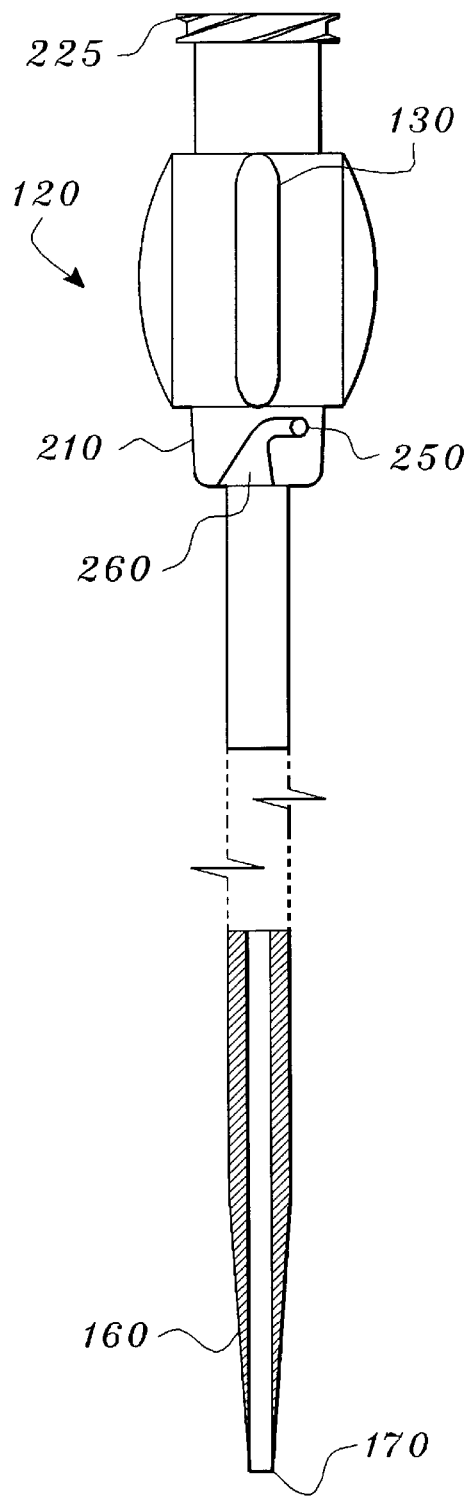
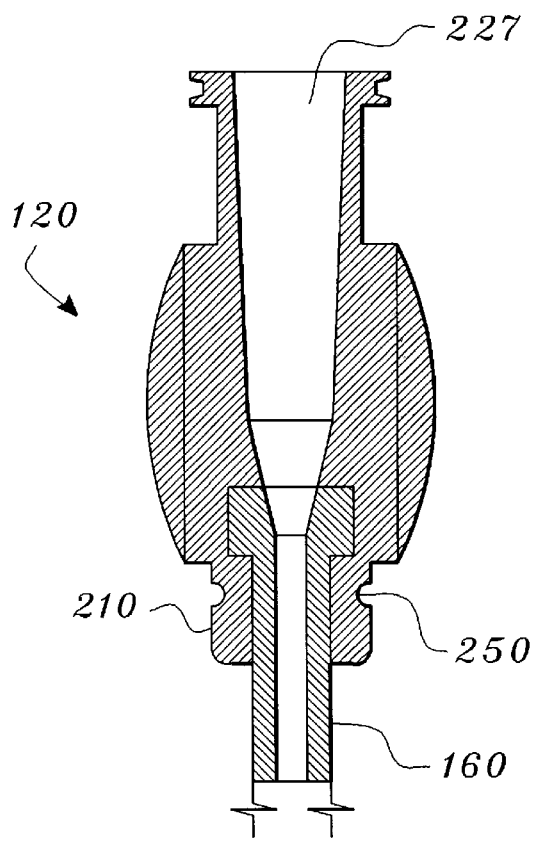
Fig. 2
Fig. 3

RELEASABLE INTERLOCK ASSEMBLY HAVING AXIAL AND ROTATIONAL ENGAGEMENT

BACKGROUND

The present invention relates to releasable interlock assemblies, particularly to those used in medical devices such as catheter introducer assemblies, catheter introducer-to-accessory assemblies, and catheters which generally comprise two or more portions, each of which must releasably engage with the other. The present invention relates particularly to elective engagements where the axial engagement between the portions must withstand forces urging the portions to separate from one another.

Catheter introducers provide a reusable conduit for the passage of guide wires, catheters, pacemaker leads, or other medical devices, e.g. biopsy instruments, through the skin, flesh, and vessel walls to gain access into blood vessels or other body passageways and cavities. Many types of accessories are used in conjunction with catheter introducers, such as hemostasis valves, Tuohy-Borst adapters, and aseptic catheter shields These accessories must by necessity couple to the catheter introducer or each other, or both, in some combination. This invention is directed to providing a simple and secure means of releasably coupling any combination of these and other devices to one another.

In typical use, say for introducing a catheter into a blood vessel, a physician inserts a needle through the body flesh and into a blood vessel, and then inserts a guide wire in to the blood vessel through the center passage of the needle. The needle is then removed leaving the guide wire in place. The introducer assembly is then inserted over the guide ire such that the tapered distal portion of the dilator acts to gradually expand the puncture opening to ease the pas sage of the introducer sheath into the blood vessel. After the introducer sheath has been inserted to a desired depth within the blood vessel, the dilator portion is removed from within the introducer portion. In this disclosure, "proximal" refers to the portions of an introducer nearest to the physician or health care worker performing the insertion procedure, and "distal" refers to the portions of the introducer nearest to, or inside of, the human or animal patient receiving the catheter.

During the initial insertion of the introducer assembly, the body's resistance to the expansion of the puncture opening exerts forces on the distal portion of the dilator tending to push the dilator distal end rearwardly in the proximal direction into the introducer sheath. In order to ensure that the tapered distal portion of the dilator remains extended beyond the blunt distal end of the introducer sheath during the initial insertion the introducer assembly, the dilator hub should be connected to the introducer hub to prevent relative axial movement of the two portions. It is important that the dilator hub and the introducer hub not disengage during the insertion procedure, but be capable of being disengaged when desired.

Catheter introducers of various forms exist in the prior art. Such devices generally consist of: (1) a dilator comprised of an elongated flexible tube with a hub permanently affixed to the proximal end. The distal end of the tube is fashioned into a generally conical tapered tip. (2) an introducer comprised of an elongated flexible tube or sheath with a hub permanently affixed to the proximal end and a distal tip which is fashioned in such a way as to minimize the resistance to insertion and trauma to the body tissue. The introducer interior diameter is sized to slidably accommodate the exterior of the dilator tube, since the two are inserted into the body as a set.

As a set, the dilator resides within the introducer, and while assembled, the distal tip of the introducer resides axially proximal to the proximal end of the tapered end of the dilator. As the name would suggest, the purpose of the dilator is to dilate or enlarge a hole in the body tissues so as to allow entry of the tubular portion of the introducer. This dilation is accomplished by means of the conical tip of the dilator which, as it is progressively inserted into the body, stretches the tissue radially outward to allow entry of the distal portion of the introducer. Once the insertion is achieved, the dilator is removed and the introducer remains as a transcutaneous conduit whereby other instruments are afforded ready access into the passageway.

During the insertion process, the body tissues resist stretching, and the resistance force vector in the axial direction would cause the dilator to move axially relative to the introducer if there were no means present to prevent such relative movement. Accidental movement of the dilator relative to the introducer during the insertion process is undesirable, for if the distal tip of the introducer is allowed to extend beyond the proximal end of the dilator tip, significant trauma to the vessel and surrounding tissues would result.

Numerous means for releasably connecting the introducer to the dilator, or to connect accessories to the introducer, or to one another, are known in the prior art. Prior art means for releasably connecting the dilator hub and the introducer hub have utilized rotatably engaging studs and complimentary slots, tapered fits, exterior clips, and ring and collar mechanisms. Many of these devices either require a significant effort to engage the locking mechanism, or do not prevent the portions from accidentally disengaging, or leave exposed protrusions on one or more members which can snag and tear a surgical glove.

The present invention solves the problems associated with prior art devices by generally providing an axial coupling means with an improved rotatably engaging releasable interlock between the dilator and introducer portions of an introducer assembly. It reduces the risk of inadvertent disengagement while minimizing the effort required for proper deployment and eliminates externally protruding portions. Additionally, all protrusions, grooves, and parts of the locking mechanism are internal when the releasable interlock is engaged, thus eliminating the risk that such parts could snag and tear a surgical glove.

SUMMARY

The present invention describes an improvement of a rotatably engaging axial coupling connection between at least two constituents of a medical device, such as between a dilator hub and an introducer hub of a catheter introducer, although the scope of application of this invention is not limited to the example.

The releasable interlock assembly with axial and rotational engagement has a first portion having a generally cylindrical or conical male member at the engaging end with one or more radially disposed grooves which engage a second portion. The second portion has a generally cylindrical or conical female member at the engaging end dimensioned so as to receive the male member of the first portion. The female portion has one or more protrusions which extend from the interior wall of the tapered female member, or socket, radially inward towards the common longitudinal axis of the two portions and which engage and cooperate with the grooves of the first portion. Upon axial engagement of the two portions, male member into female member, one portion is rotated relative to the other portion causing the protrusions in the second portion to enter engagement with the grooves of the first portion. Upon continued rotation, the protrusions of the second portion encounter a dimensional interference with the grooves of the first portion. Upon continued rotation, and with a greater amount of applied torque required, one or both of the portions elastically deform into a stressed condition so as to overcome the dimensional interference thus allowing continued relative rotational motion between the two portions.

With continued applied torque, this relative rotational motion is sustained, with one or both portions in a stressed condition, until the inwardly radially directed protrusions of the second portion come to a blind end of the grooves of the first portion at which point the dimensional interference between the two portions is significantly reduced. This represents the releasably locked state of engagement between the two portions. The sudden reduction of dimensional interference and subsequent stress relaxation provides a tactile sensation thus signaling the user that the releasably locked state has been achieved. Only by reversing the amount and direction of applied torque and retracing the original path of the protrusions within the grooves can the interference fit be defeated and disengagement of the two members achieved.

The preferred embodiment of this invention achieves the engagement and disengagement within a ninety-degree range of rotation. The preferred embodiment of this invention would be comprised of portions with generally elastic, but resilient, materials which will elastically deform at the strain represented by the interference fit overcome, but would possess a relatively high stiffness and natural frequency of vibration so as to spring back into their unstressed state with a minimum of damping. Some of the suitable materials would be polypropylene or acrylonitril butadine styrene (ABS), or metals having these characteristics.

DESCRIPTION OF THE DRAWINGS

FIG. 2 is an side view of dilator portion of the introducer assembly showing the portion of the locking mechanism associated with the dilator hub.

FIG. 3 is a sectional view of the dilator portion depicted in FIG. 2.

DESCRIPTION OF THE PREFERRED EMBODIMENTS

The following description will disclose an embodiment of the invention in the context of a catheter introducer. However, this is intended to be illustrative only. The invention is not limited to applications in catheter introducers, and is applicable to other medical devices, as the reader will see.

Figure 1:
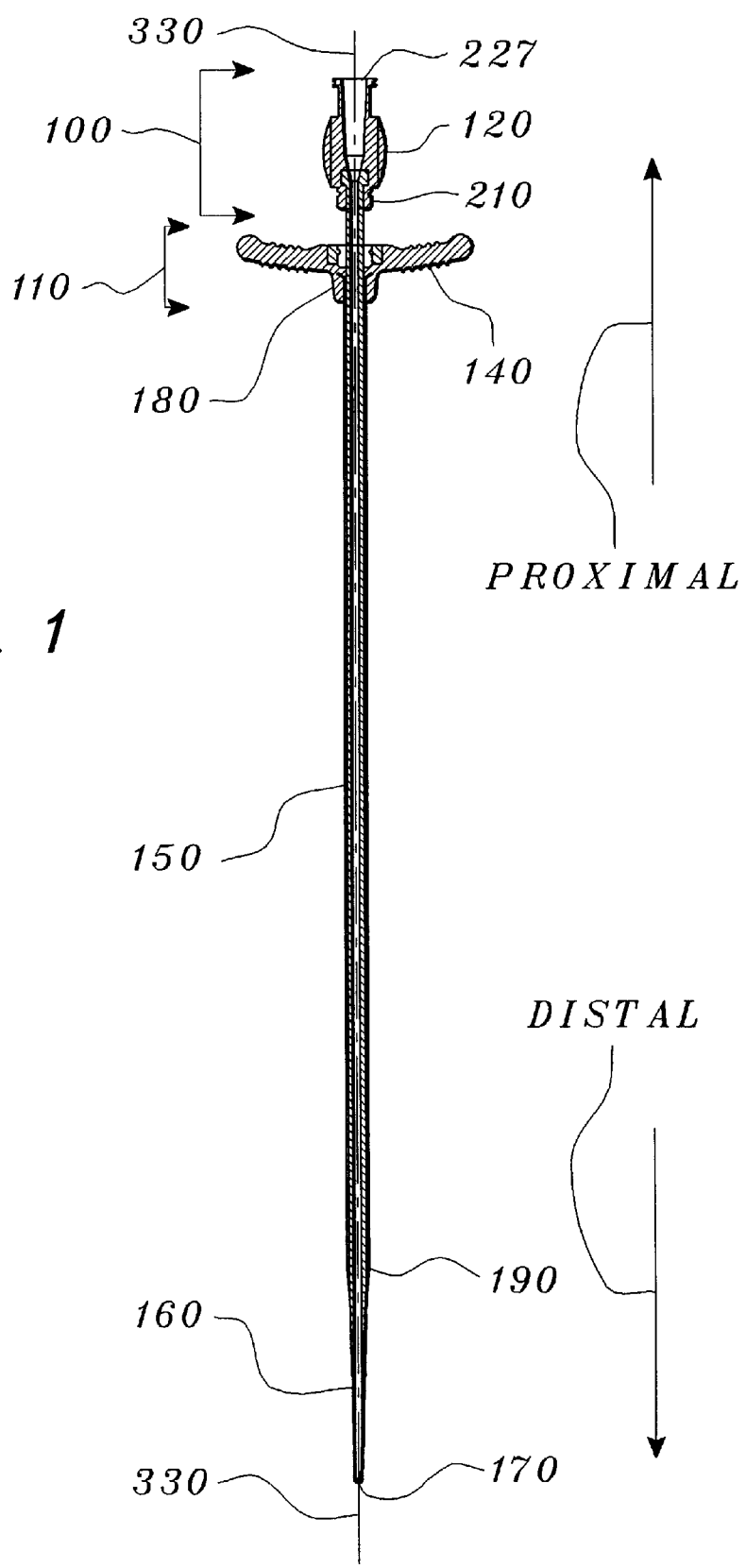
FIG. 1 is a cross-sectional view of the preferred embodiment of the improved catheter introducer which depicts the two major portions axially disengaged from their locked state.

Referring to FIG. 1, the catheter introducer assembly comprises a dilator portion 100 and an introducer portion 110. The dilator portion 100 comprises a dilator hub 120 and a dilator tube 160 with a conical tapered distal tip 170. The introducer portion is comprises an introducer hub 180 and an introducer tube 150 with a tip 190 fashioned onto the distal end. The introducer portion and the dilator portion are shown partly disengaged and unlocked in FIG. 1. FIG. 1 also shows the common longitudinal axis 330 of the dilator portion 100 and the introducer portion 110.

FIG. 2 shows the dilator of the preferred embodiment, comprising a hub 120 and a tube 160. The dilator hub 120 includes a conically tapered male member 210 disposed on the distal end of the hub. In the preferred embodiment, the male member 210 is an integral part of the dilator hub 120, is symmetric about the longitudinal axis of the hub, and is dimensioned to establish a slip fit relationship when fully engaged with the female member 220 of the introducer hub 180 (See FIG. 5). In the preferred embodiment, two grooves 260 are disposed on the male member 210, with each of the grooves 260 having an open end 270 and a blind end 280. In the preferred embodiment, the two grooves 260 are identical in geometry and axial location and positioned 180 degrees apart in radial orientation. The grooves 260 are oriented to require a clockwise rotation of the dilator hub 120 within the introducer hub 180 when viewed from the proximal end, so as to cause a locking engagement between the introducer hub 180 and the dilator hub 120. The open end 270 of each groove 260 is distally disposed and broadened at the open end to readily receive the complementary protrusions 240 on the introducer hub 180 (see FIGS. 4 and 5) upon insertion of the dilator hub 120 into the introducer hub 180.

Figure 4:
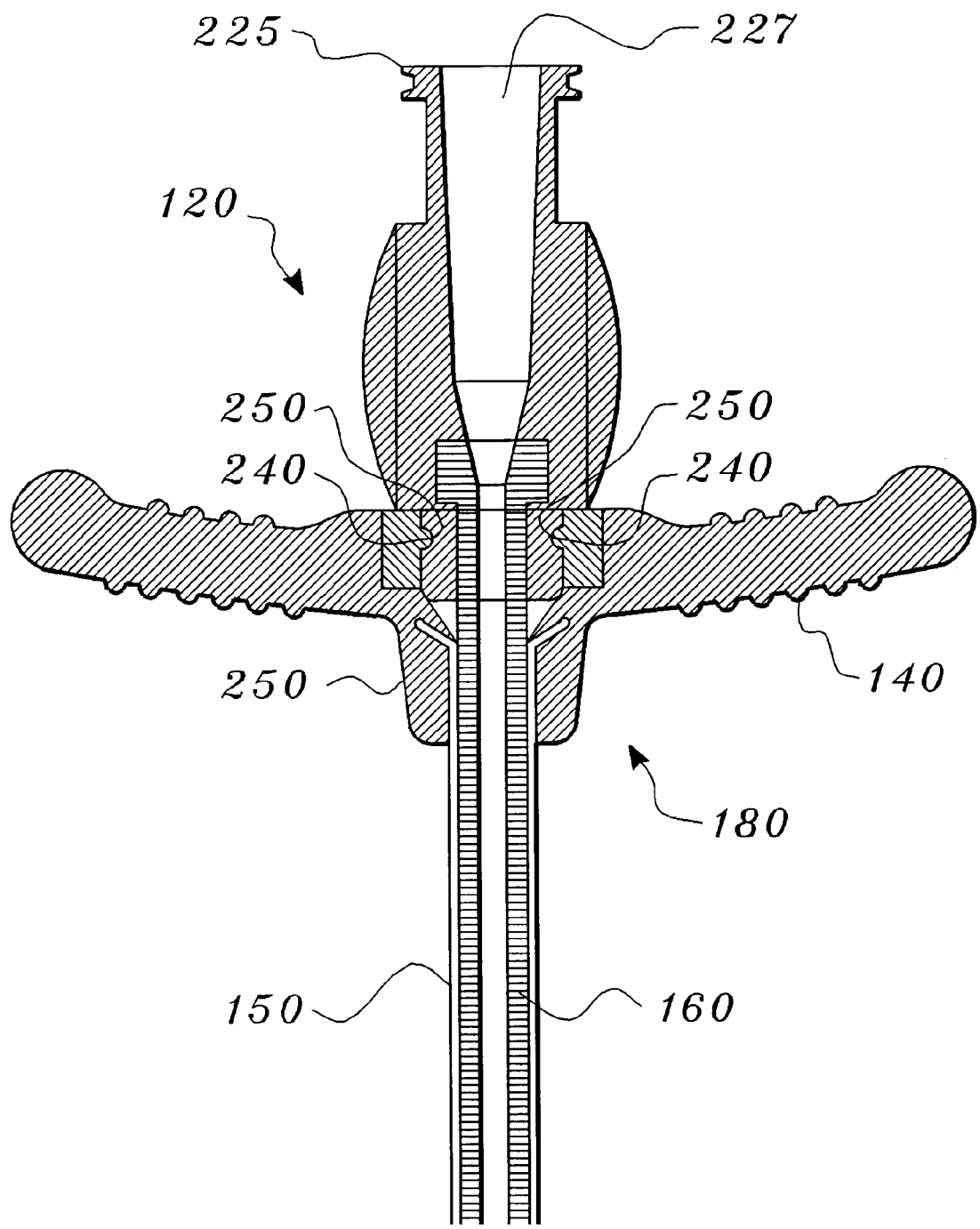
FIG. 4 is an enlarged sectional view of the dilator and introducer portions of the preferred embodiment showing the two portions engaged.
Figure 5:
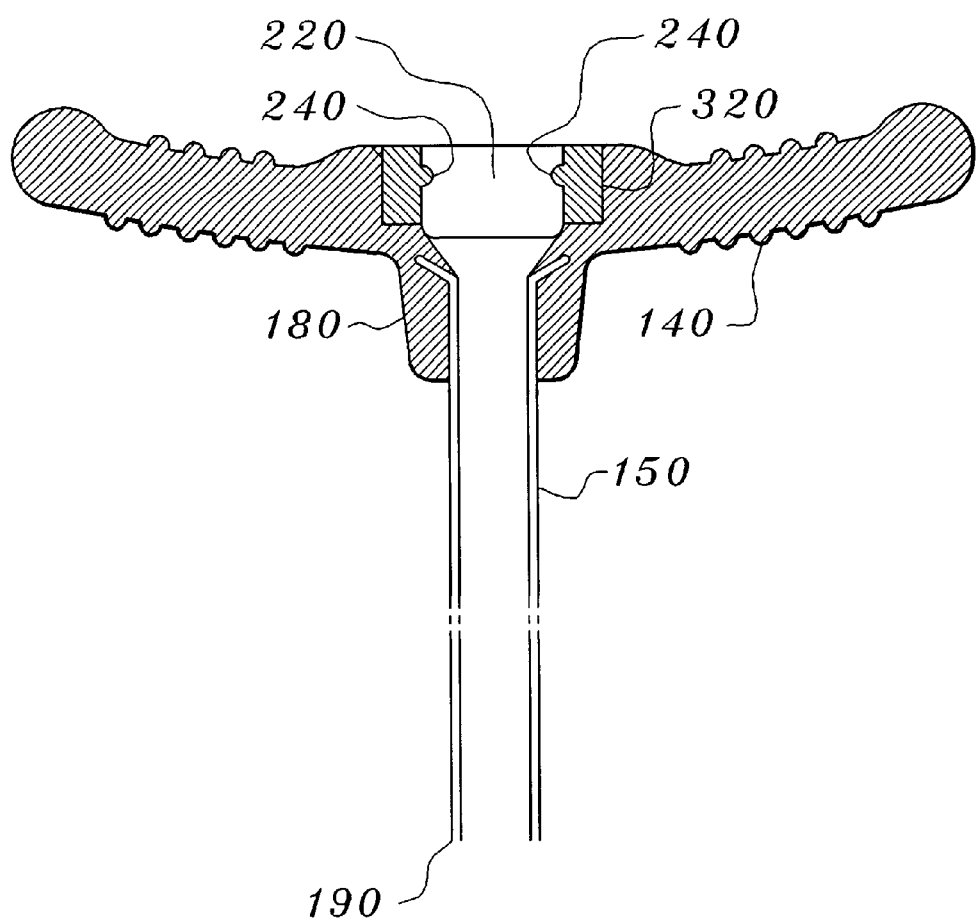
FIG. 5 is sectional side view of the introducer portion of the preferred embodiment.

FIGS. 4 and 5 more clearly show the protrusions 240 on the interior wall of the introducer hub engaged with the pockets 250 in the dilator hub. The two portions are depicted in the mechanically interlocked state in FIG. 4.

Tracing the groove 260 from its broad distal opening 275 proximally, the width of the groove 260 decreases until it enters the distal opening of the groove knee 290 where the groove transitions from being generally axially aligned to generally circumferentially aligned. That is, the groove 260 has a generally axially aligned portion 295 and a generally circumferentially aligned portion 300. At the distal opening of the knee 290, the width is slightly greater than the greatest width of the introducer hub protrusion 240. Similarly, as the width of the groove 260 diminishes, the radial distance to the bottom of the grooves as measured from the longitudinal axis 330 of the dilator hub 120 increases until the radial distance from the bottom of one groove 260 to the bottom of the other groove 260 is slightly less than the minimum radial distance from one introducer hub protrusion 240 to the other. Continuing to trace the groove 260 along the knee 290 in a proximal and increasingly radial direction, the distance from the bottom of the groove 260 to the longitudinal axis 330 of the dilator hub 120 (which is also the axis of rotation of the dilator hub 120) increases until the distance from the bottom of one groove 260 to the bottom of the other groove 260 is greater than the minimum radial distance from one introducer hub protrusion 240 to the other.

It would be possible to implement the invention with only one groove 260 and one complementary protrusion 240, although the best mode for practicing the invention requires the use of at least two, or more, complementary grooves 260 and protrusions 240. In the case of one groove 260, and one protrusion 240, it may be explained that the distance from the bottom of the groove 260 from the longitudinal axis 330 of the introducer hub (which is also the axis of rotation of the introducer hub) is greater than the radial distance from the longitudinal axis 330 of the dilator hub to the protrusion, at a point before the pocket 250. And, the radial distance of the bottom of the pocket 250 from the longitudinal axis 330 of the introducer hub 180 is equal to or less than the radial distance from the longitudinal axis 330 of the introducer hub 180 to the protrusion 240, so that the introducer hub 180 and the dilator hub 120 are again inhibited from axial and rotational disengagement.

Continuing to trace the groove 260 around its now generally circumferential portion 300 about the male member 210, the radial spacing between grooves 260 continues until the blind end 280 of the groove 260 is approached. A pocket 250 is disposed at the blind end 280 of the groove 260. In the preferred embodiment, the radial distance between the bottom of each pocket 250 in each of the two grooves 260 is equal to or less than the minimum radial distance from one introducer hub protrusion 240 to the other. The pocket 250 is otherwise designed geometrically to receive the complementary protrusion 240 on the introducer hub 180. The axial distance separating the pocket 250 from the proximal end of the male member 210 of the dilator hub 120 is sufficient to allow for a fall locking engagement of the dilator hub 120 into the introducer hub 180 without causing dimensional interference between the two hubs 120 and 180 in the axial direction. In the preferred embodiment, the dilator hub 120 includes fins 130 to facilitate a greater degree of fingertip control by the user when locking or unlocking the dilator hub 120 with the introducer hub 180.

Figure 6:
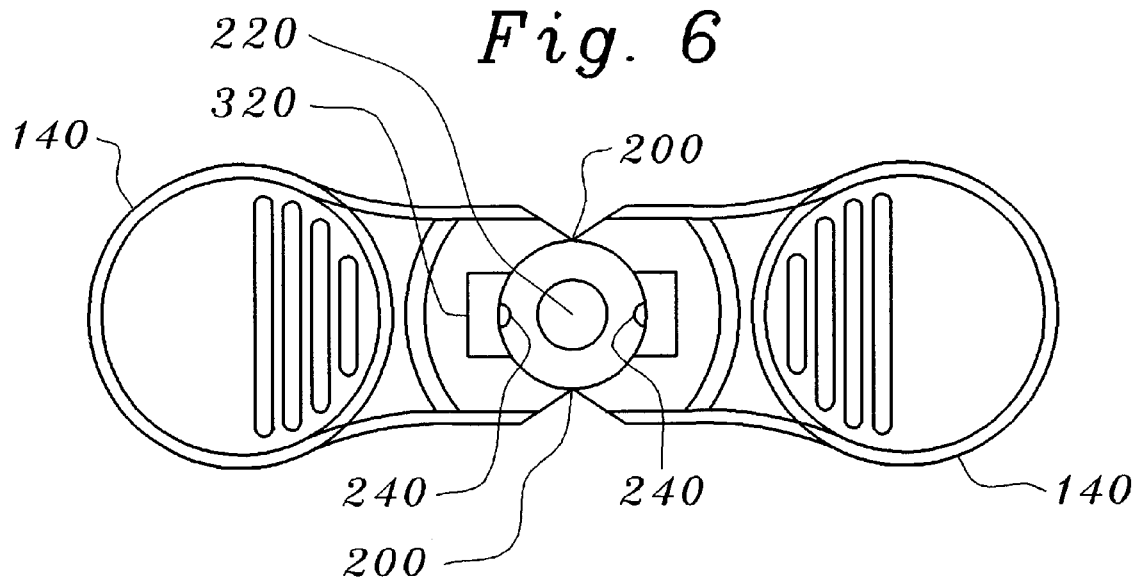
FIG. 6 is an end view of the introducer portion of the preferred embodiment.

Referring to FIGS. 5 and 6, the introducer portion 110 of the preferred embodiment comprises a hub 180 and an introducer tube 150. The introducer tube 150 is sized to allow for easy passage over the dilator tubing 160. Proximally disposed in the introducer hub 180 is a conically tapered female member 220 dimensioned to establish a slip fit relationship when fully engaged with the conical male member 210 of the dilator hub 120. Two protrusions 240 are disposed in the proximal end of the female member 220. Each protrusion 240 is directed inwardly toward the long axis of the hub, and faces the other protrusion. The protrusions 240 may be an integral part of the introducer hub 180 or may be included as inserts 320 which are permanently attached to the introducer hub 180, depending on the actual manufacturing method and materials chosen. In FIGS. 5 and 6, they are shown incorporated into inserts 320, which are permanently affixed within the introducer hub 180. Each protrusion 240 is positioned within the introducer hub 180 in the same location axially and at the same distance from the longitudinal axis 330 of the hub 180 thus forming a symmetrical relationship. The distance separating the protrusions 240 from the proximal end of the hub 180 is sufficient to allow for a full locking engagement of the dilator hub 120 into the introducer hub 180 without causing dimensional interference between the two hubs 120 and 180 in the axial direction.

Figure 7:
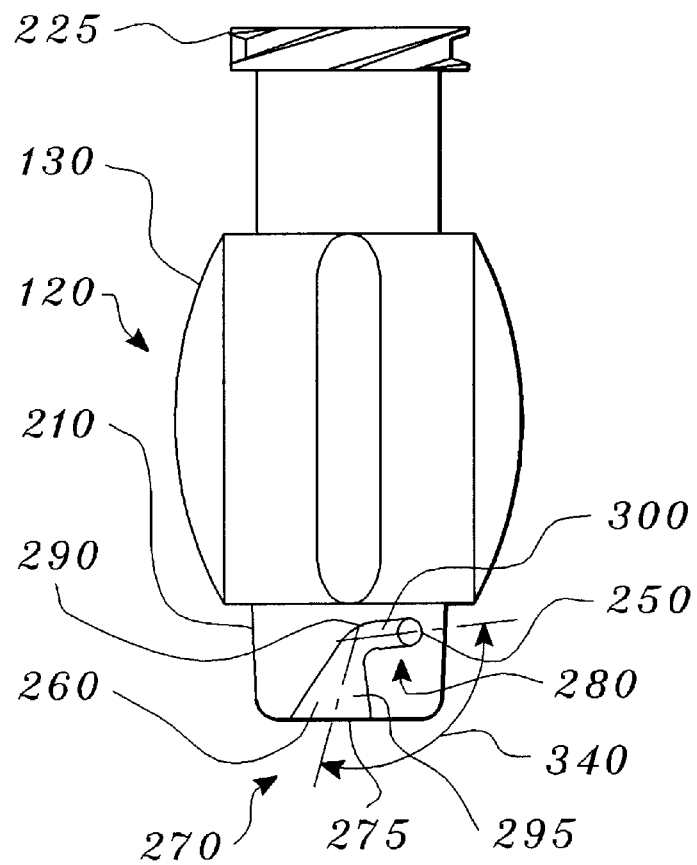
FIG. 7 is a side view of the dilator hub of the preferred embodiment, showing the groove and pocket which cooperate with the protrusions of the introducer hub.
Figure 8:
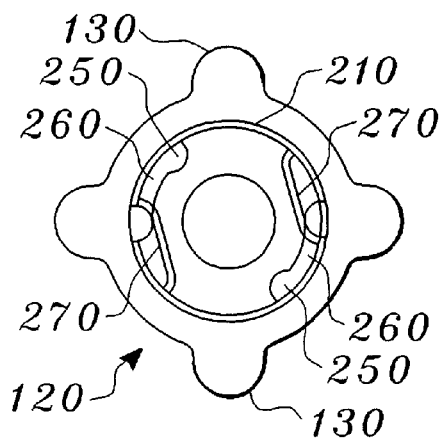
FIG. 8 is an end view of the dilator hub.
Figure 9:
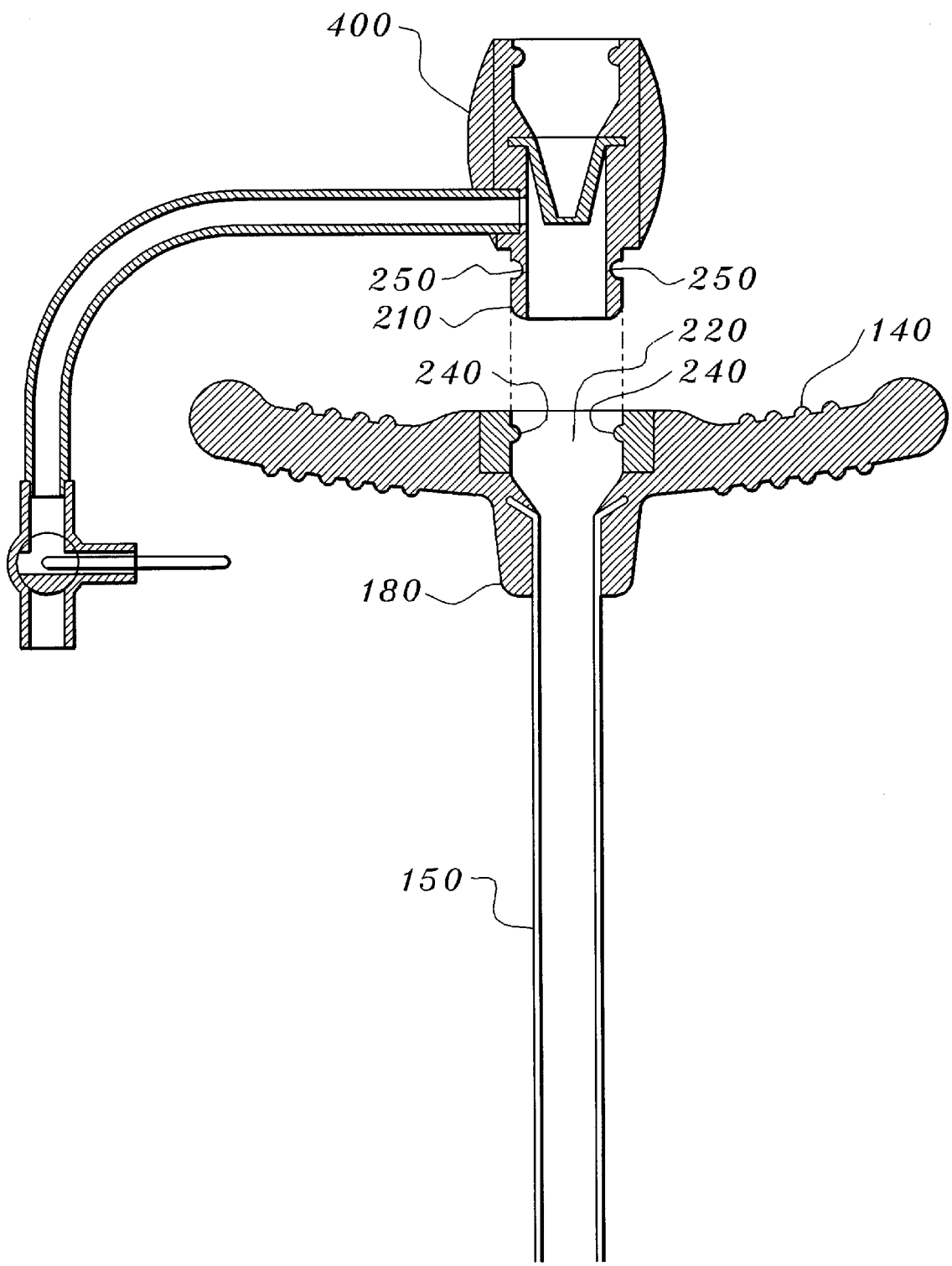
FIGS. 9, 10, 11, and 12 show, respectively, a hemostasis valve, a Tuohy-Borst adapter, an aseptic shield assembly, and an obturator, each connecting to the female portion of an introducer by means of the preferred embodiment.
Figure 10:
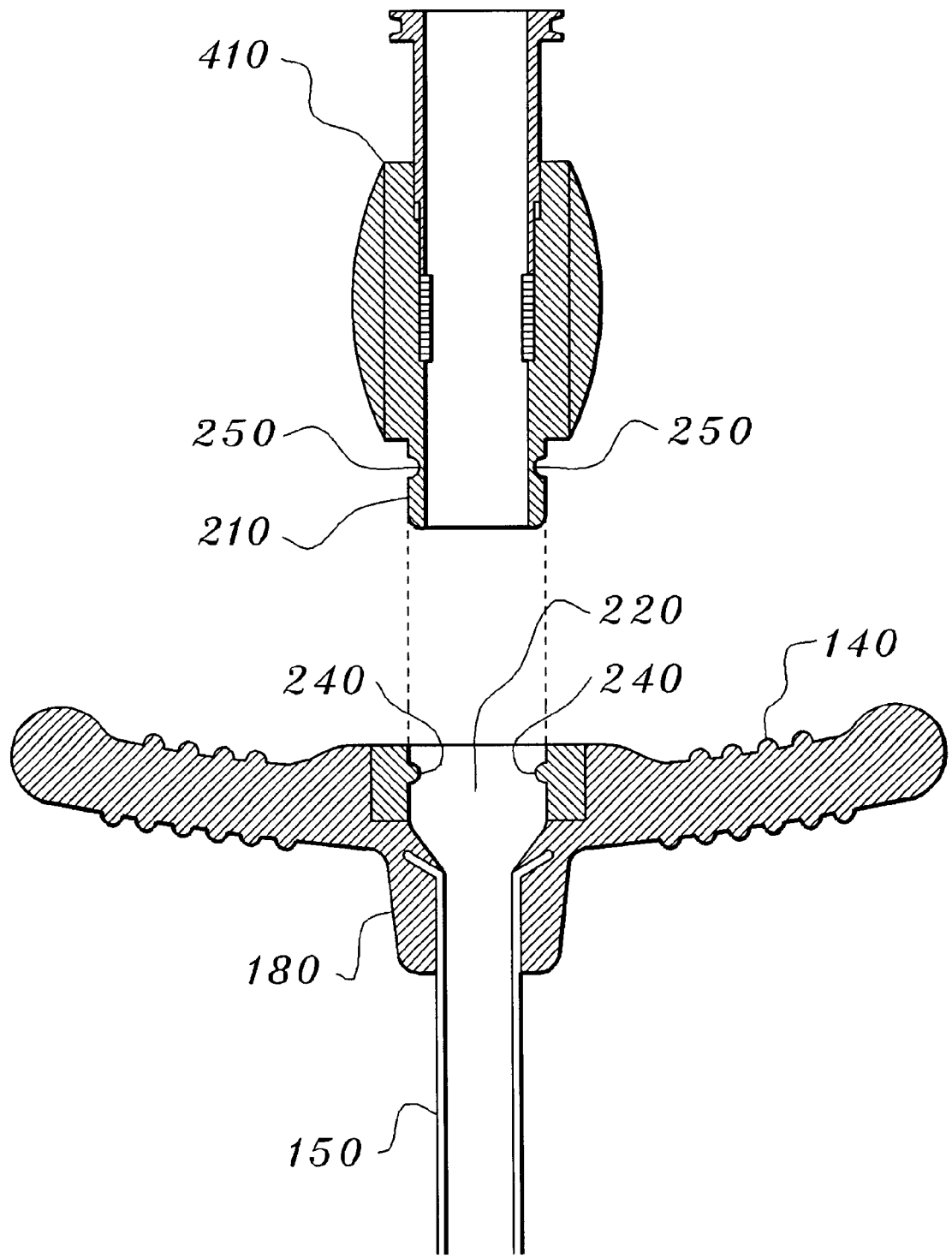
Figure 11:
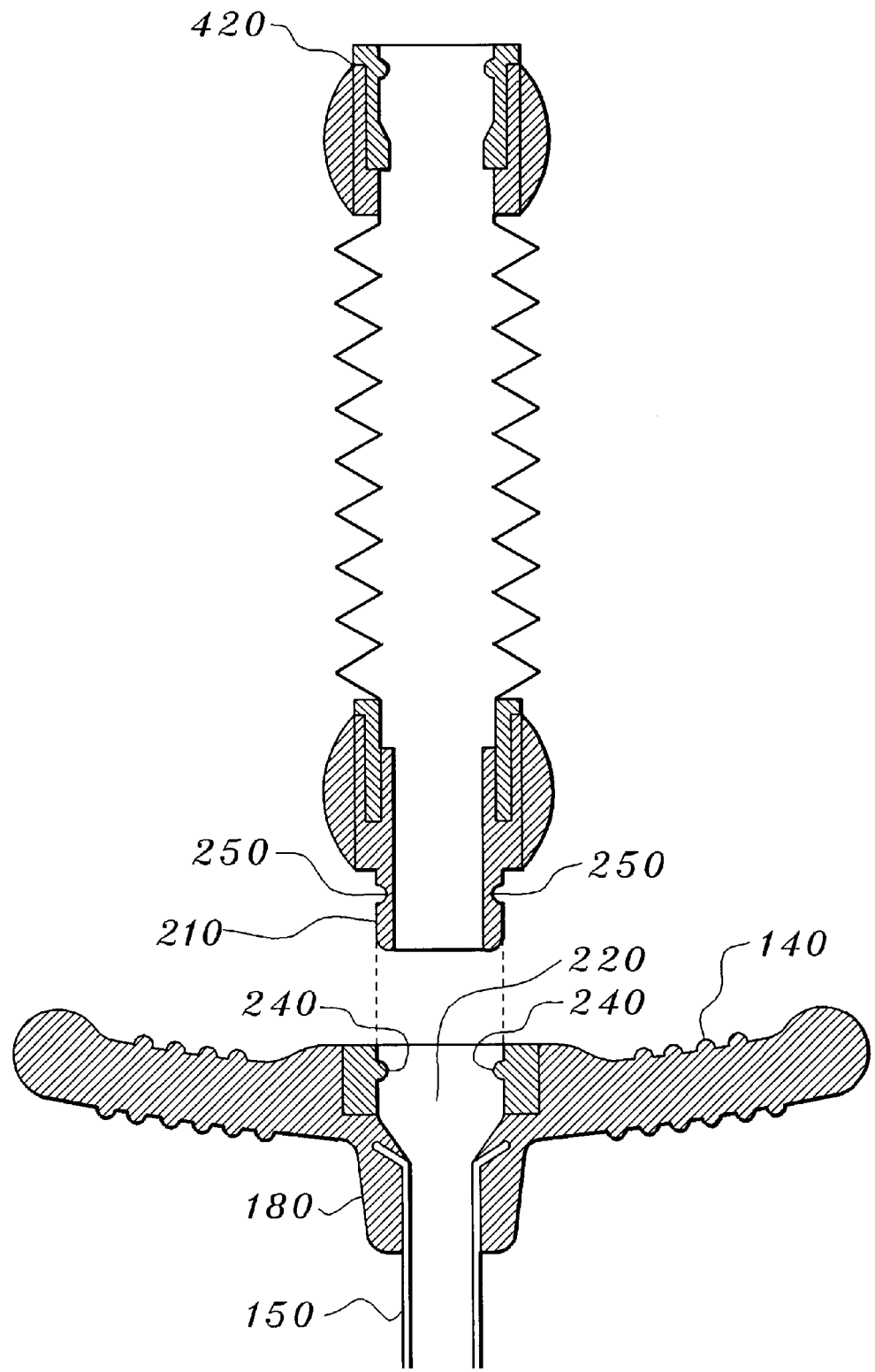
Figure 12:
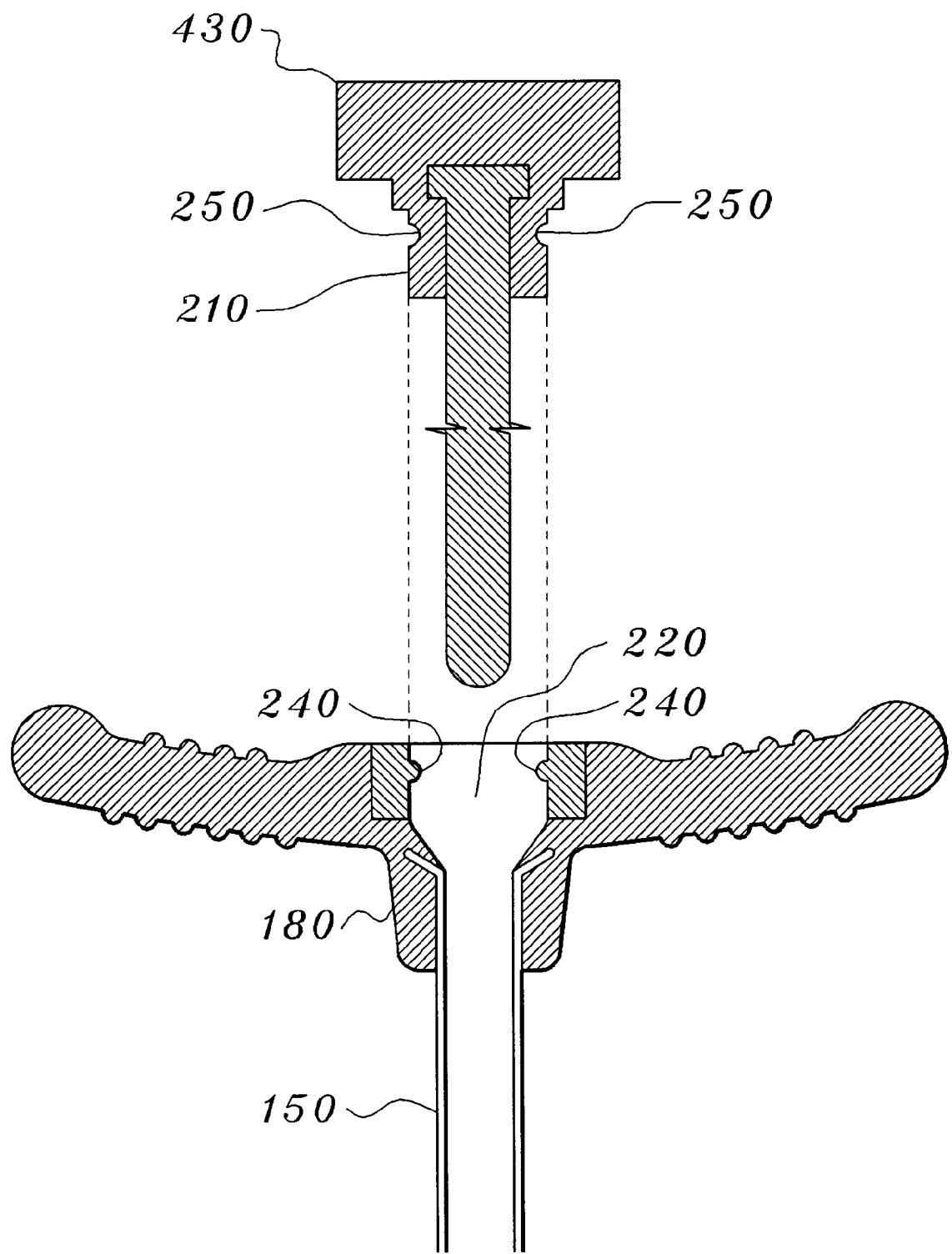

The dilator hub 120 and the introducer hub 180 are mechanically interlocked by first introducing the distal end of the dilator tube 160 into the proximal end of the introducer hub 180 and engaging the two axially until the distal end of the male member 210 of the dilator hub enters the female member 220 of the introducer hub 180. Next, the user orientates the open ends of the dilator hub grooves 260 radially until they align with the protrusions 240 in the introducer hub 180, to make possible further axial engagement. Upon further axial engagement, the grooves 260 engage and slidably cooperate with the introducer protrusions 240 until the protrusions 240 approach the knee 290 of the grooves 260, at which point a combination of axial and radial relative motion is necessary to continue engagement. At the radially disposed point of the knee 290, the relative movement between the two hubs 120 and 180 is generally radial and the protrusions 240 ramp into a state of dimensional interference. Further rotation causes compression in the outward radial direction of the introducer hub 180 via the protrusions 240, and to a lesser extent a deflection in the inward radial direction of the dilator hub 120. This deflection allows the further passage of the protrusions 240 along and within the grooves 260, although the hubs 120 and 180 are now in a state of compressive stress and require a greater amount of torque to defeat the increased friction between the sliding surfaces and allow continued rotation. Once the protrusions 240 reach the blind end 280 of the grooves 260, the dimensional interference between the two hubs 120 and 180 is substantially and rapidly reduced, and the stressed condition between the hubs 120 and 180 is relieved as the protrusions 240 fall into the pockets 250 and thus engage in the locked position. This rapid decompression caused by the protrusions 240 falling into engagement with the pockets 240 creates a tactile sensation to the user and provides a signal to the user that the locked condition has been achieved. The hubs 120 and 180 will remain in the locked position until the user reverses the engagement process. In the preferred embodiment of the invention, as shown in FIG. 7, the circumferential portion 300 of the grooves 260 is disposed at an angle, α, 340 greater than 90 degrees with the generally axial portion of the grooves 260, which tends to urge the tapered male member 210 of the dilator hub 160 firmly into the tapered female member 220 of the introducer hub 180. In the preferred embodiment this angle 340 is 92 degrees, or 2 degrees from the centerline of the circumferential portion 300 of each groove 260.

As shown in FIG. 6, the introducer hub 180 preferably has a handle 140. Removal of the introducer tube 150 may be accomplished by conventional means, such as the splitting away of the introducer tube 150, which may have been pre-scored to allow this action. In this case, the handle 140 is constructed so as to allow the operator to grasp its two arms and break it in two along intentionally weakened areas 200, thus beginning splits which remove the introducer tube 150 from the catheter or other medical device inserted into the body. In the preferred embodiment the dilator hub 120 has a conventional connection to other medical equipment. A Luer thread 225 and Luer taper 227 are shown in FIGS. 4 and 7.

The reader should understand that the invention is not limited to the catheter introducer described above. As shown in FIGS. 9–12, the hub 120 previously shown connected to a dilator portion 100 can be connected to other medical devices. Examples are the hub 120 containing the tapered male member 210 having the grooves 260 and pockets 250 previously described connected to a hemostasis valve 400, a Tuohy-Borst adapter 410, an aseptic catheter shield 420, and an obturator 430. Once the introducer portion 110 is in place within the desired blood vessel or body cavity, one of these instruments may be interchangeably connected to it.

The need for a mechanically simple yet secure introducer assembly capable of being releasably locked and disengaged has been attained by the present invention, as described above. Since certain changes could be made in the embodiment of the invention described above without departing from the spirit and scope of the invention, I intend that all matter contained in the foregoing description and drawings shall be interpreted as illustrative and not in a limiting sense. The reader should understand that the following claims are intended to cover all of the generic and specific features of the invention described in this application, and all statements of the scope of the invention which might be interpreted to fall between these features.

I claim:

1. A releasable interlock assembly comprising:
   a. a longitudinal axis;
   b. a male member having a proximal end and a distal end;
   c. a female member having a proximal end and a distal end, the female member sized to receive the distal end of the male member without dimensional interference;
   d. at least one groove associated with the male member; the groove further comprising:
      (1) an open end and a blind end, the open end distally disposed;
      (2) a first portion generally axially aligned with the longitudinal axis, and a second portion generally circumferentially aligned with the male member, and a knee defining the transition from the first portion to the second portion; and,
      (3) a pocket associated with the blind end of the groove;
   d. at least one protrusion associated with the female member for complementarily engaging the groove; and,
   e. the groove, where the depth of the groove decreases as the groove is traversed from the open end to the blind end, so that the radial distance from the bottom of the groove to the longitudinal axis is greater than the radial distance from the longitudinal axis to the protrusion at a point before the pocket; and,
   f. the pocket, where the radial distance of the bottom of the pocket from the longitudinal axis is equal to or less than the radial distance from the longitudinal axis to the protrusion,
so that the male member and female member are inhibited from axial and rotational disengagement when the protrusion rests in the pocket.

2. The releasable interlock assembly of claim 1 where the second portion of the groove generally circumferentially aligned with the male member makes an angle greater than 90 degrees with the corresponding first portion of the groove generally axially aligned with the longitudinal axis.

3. The releasable interlock assembly of claim 1 where the male member is further connected to a medical device.

4. The releasable interlock assembly of claim 3 above where the medical device is a hemostasis valve.

5. The releasable interlock assembly of claim 3 above where the medical device is a Tuohy-Borst adapter.

6. The releasable interlock assembly of claim 3 above where the medical device is an aseptic catheter shield.

7. The releasable interlock assembly of claim 3 above where the medical device is an obturator.

8. A releasable interlock assembly comprising:
   a. a longitudinal axis;
   b. a male member having a proximal end and a distal end;
   c. a female member having a proximal end and a distal end, the female member sized to receive the distal end of the male member without dimensional interference;
   d. two grooves associated with the male member; each groove further comprising:
      (1) an open end and a blind end, the open end distally disposed;
      (2) a first portion generally axially aligned with the longitudinal axis, and a second portion generally circumferentially aligned with the male member, and a knee defining the transition from the first portion to the second portion; and,
      (3) a pocket associated with the blind end of each groove;
   d. two protrusions associated with the female member, each complementarily engaging one of the grooves; and,
   e. the grooves, where the radial distance from the bottom on one groove to the bottom of the other groove increases as the grooves are traversed from the open end to the blind end and the radial distance from the bottom of one groove to the bottom of the other groove is greater than the radial distance of one protrusion from the other protrusion at a point before the pockets; and,
   f. the pocket, where the radial distance of the bottom of each pocket is equal to or less than the radial distance from one protrusion to the other;
so that the male member and female member are inhibited from axial and rotational disengagement when the protrusions rest in the pockets.

9. The releasable interlock assembly of claim 8 where the second portion of each groove generally circumferentially aligned with the male member makes an angle greater than 90 degrees with the corresponding first portion of each groove generally axially aligned with the longitudinal axis.

10. The releasable interlock assembly of claim 8 where the male member is further connected to a medical device.

11. The releasable interlock assembly of claim 10 above where the medical device is a hemostasis valve.

12. The releasable interlock assembly of claim 10 above where the medical device is a Tuohy-Borst adapter.

13. The releasable interlock assembly of claim 10 above where the medical device is an aseptic catheter shield.

14. The releasable interlock assembly of claim 10 above where the medical device is an obturator.

15. The introducer of claim 14 where the groove is associated with the male member, and the protrusion is associated with the female member.

16. The introducer assembly of claim 14 where the groove has an open end and a blind end.

17. The introducer assembly of claim 14 where the groove has a knee portion; the knee portion defining the transition of the groove from generally axial alignment with the longitudinal axis of the introducer assembly to generally circumferential alignment with the longitudinal axis of the introducer assembly.

18. The introducer assembly of claim 16 where the blind end of the groove has a pocket for receiving the protrusion.

19. The introducer assembly of claim 16 where the blind end of the groove is associated with the generally circumferentially aligned portion of the groove.

20. The introducer assembly of claim 16 where the open end of the groove is associated with the generally axially aligned portion of the groove.

21. The introducer assembly of claim 16 where the open end of the groove is distally disposed.

22. The introducer assembly of claim 16 where the open end of the groove is wider than the blind end of the groove.

23. The introducer assembly of claim 16 where the tapered female member is sized to receive the tapered male member without dimensional interference in the axial direction when the dilator hub and introducer hub are releasably locked together.

24. The introducer assembly of claim 16 where the depth of the groove decreases as the groove is traversed from the open end to the blind end.

25. The introducer assembly of claim 18 where the radial distance from the bottom of the groove from the longitudinal axis is greater than the radial distance from the longitudinal axis to the protrusion at a point before the pocket.

26. The introducer assembly of claim 25 where the radial distance of the bottom of the pocket from the longitudinal axis is equal to or less than the radial distance from the longitudinal axis to the protrusion, so that the introducer hub and the dilator hub are inhibited from axial and rotational disengagement when the protrusion rests in the pocket.

27. The introducer assembly of claim 14 where the second portion of the groove generally circumferentially aligned with the longitudinal axis of the introducer assembly makes an angle greater than 90 degrees with the first portion of the groove generally axially aligned with the introducer assembly.

28. The introducer assembly of claim 27 where each groove has an open end, and a blind end, the open end of each groove being wider than the blind end of the groove, and a knee; the knee defining the transition of the groove from generally axial alignment with the introducer assembly to generally circumferential alignment with the introducer assembly.

29. The introducer assembly of claim 28 where the blind end of each groove is associated with the generally circumferentially aligned portion of the groove, the open end of each groove is associated with the generally axially aligned portion of the groove, and distally disposed, and the blind end of each groove has a pocket for receiving one of the protrusions.

30. The introducer assembly of claim 29 where the tapered female member is sized to receive the tapered male member without dimensional interference in the axial direction when the dilator hub and introducer hub are releasably locked together.

31. The introducer assembly of claim 30 where
   a. the radial distance from the bottom of one groove to the bottom of the other groove increases as the grooves are traversed from the open end to the blind end;
   b. the radial distance from the bottom of one groove to the bottom of the other groove is greater than the radial distance of one protrusion from the other protrusion at a point before the protrusions reach the pockets;
   c. the radial distance between the bottom of each pocket is equal to or less than the radial distance from one protrusion to the other;
so that the introducer hub and the dilator hub are inhibited from axial and rotational disengagement, when each protrusion rests in a pocket.

32. The introducer assembly of claim 31 where the second portion of each groove generally circumferentially aligned with the longitudinal axis of the introducer assembly makes an angle greater than 90 degrees with the corresponding first portion of each groove generally axially aligned with the introducer assembly.

33. An introducer having a releasable interlock assembly, and a longitudinal axis, the introducer comprising:
   a. a dilator portion, the dilator portion having a proximal end and a distal end; the dilator portion further comprising a dilator tube having a proximal end, a distal end, and a tapered distal portion;
   b. an introducer portion, the introducer portion having a proximal end and a distal end; the introducer portion further comprising an introducer tube having a proximal end and a distal end; the introducer portion sized to slidably receive the dilator tube;
   c. a dilator hub disposed at the proximal end of the dilator portion;
   d. an introducer hub disposed at the proximal end of the introducer portion;
   e. a means complementarily associated with the dilator hub and the introducer hub for releasably locking together the dilator hub and the introducer hub so as to inhibit both axial and rotational disengagement of the dilator hub and the introducer hub; the means for releasably locking the dilator hub and the introducer hub further comprising:
      (1) a tapered male member associated with the dilator hub and a tapered female member associated with the introducer hub;
      (2) at least one groove associated with the tapered male member, the groove having a first portion generally axially aligned with the introducer assembly, and a second portion generally circumferentially aligned with the introducer assembly, so that the second portion of the groove generally circumferentially aligned with the longitudinal axis of the introducer assembly makes an angle greater than 90 degrees with the first portion of the groove generally axially aligned with the introducer assembly;
      (3) the groove, where the groove has a knee portion; the knee portion defining a transition of the groove from general axial alignment with the introducer assembly to generally circumferential alignment with the introducer assembly;
      (4) the groove, where the groove further has a distally disposed open end, and a blind end;
      (5) at least one protrusion associated with the tapered female member for complementarily engaging the groove;
      (6) a pocket associated with the blind end of the groove for receiving the protrusion, where the radial distance of the bottom of the pocket from the longitudinal axis is equal to or less than the radial distance from the longitudinal axis to the protrusion, so that the introducer hub and the dilator hub are inhibited from axial and rotational disengagement when the protrusion rests in the pocket; and,
      (7) the groove, where the depth of the groove decreases as the groove is traversed from the open end to the blind end, so that at a point before the pocket, the radial distance from the bottom of the groove to the longitudinal axis is greater than the radial distance from the longitudinal axis to the protrusion,
so that the introducer hub and the dilator hub are inhibited from axial and rotational disengagement, when the protrusion rests in the pocket.

34. An introducer having a releasable interlock assembly, and a longitudinal axis, the introducer comprising:
   a. a dilator portion, the dilator portion having a proximal end and a distal end; the dilator portion further comprising a dilator tube having a proximal end, a distal end, and a tapered distal portion;
   b. an introducer portion, the introducer portion having a proximal end and a distal end; the introducer portion further comprising an introducer tube having a proximal end and a distal end; the introducer portion sized to slidably receive the dilator tube;
   c. a dilator hub disposed at the proximal end of the dilator portion;

d. an introducer hub disposed at the proximal end of the introducer portion;
e. a means complementarily associated with the dilator hub and the introducer hub for releasably locking together the dilator hub and the introducer hub so as to inhibit both axial and rotational disengagement of the dilator hub and the introducer hub; the means for releasably locking the dilator hub and the introducer hub further comprising:
  (1) a tapered male member associated with the dilator hub and a tapered female member associated with the introducer hub;
  (2) two grooves associated with the tapered male member, the grooves disposed radially 180 degrees apart; each groove having a first portion generally axially aligned with the introducer assembly, and a second portion generally circumferentially aligned with the introducer assembly, so that the second portion of each groove generally circumferentially aligned with the longitudinal axis of the introducer assembly makes an angle greater than 90 degrees with the associated first portion of each groove generally axially aligned with the introducer assembly;
  (3) the grooves, where each groove has a knee portion; the knee portion defining a transition of the groove from general axial alignment with the dilator assembly to generally circumferential alignment with the dilator assembly;
  (3) the grooves, where each groove further has a distally disposed open end, and a blind end;
  (4) two protrusions associated with the tapered female member disposed radially 180 degrees apart so that each protrusion may complementarily engage a corresponding groove;
  (5) a pocket associated with the blind end of each groove for receiving the protrusion, where the radial distance between the bottom of each pocket is equal to or less than the radial distance from one protrusion to the other; and,
  (6) the grooves, where the radial distance from the bottom of one groove to the bottom of the other groove is greater than the radial distance of one protrusion from the other protrusion at a point before the protrusions reach the pockets; so that the introducer hub and the dilator hub are inhibited from axial and rotational disengagement.
so that the introducer hub and the dilator hub are inhibited from axial and rotational disengagement, when each protrusion rests in a pocket.

35. An introducer having a releasable interlock assembly, and a longitudinal axis, the introducer comprising:
a. a dilator portion, the dilator portion having a proximal end and a distal end;
b. an introducer portion, the introducer portion having a proximal end and a distal end;
c. a dilator hub disposed at the proximal end of the dilator portion;
d. an introducer hub disposed at the proximal end of the introducer portion;
e. a means complementarily associated with the dilator hub and the introducer hub for releasably locking together the dilator hub and the introducer hub so as to inhibit both axial and rotational disengagement of the dilator hub and the introducer hub; the means for releasably locking the dilator hub and the introducer hub further comprising:
  (1) at least one groove, the groove having a first portion generally axially aligned with the longitudinal axis of the introducer assembly, and a second portion generally circumferentially aligned with the longitudinal axis of the introducer assembly;
  (2) at least one protrusion complementarily engaging the groove; and,
  (3) a tapered male member associated with the dilator hub and a tapered female member associated with the introducer hub.

36. An introducer having a releasable interlock assembly, and a longitudinal axis, the introducer comprising:
a. a dilator portion, the dilator portion having a proximal end and a distal end;
b. an introducer portion, the introducer portion having a proximal end and a distal end;
c. a dilator hub disposed at the proximal end of the dilator portion;
d. an introducer hub disposed at the proximal end of the introducer portion;
e. a means complementarily associated with the dilator hub and the introducer hub for releasably locking together the dilator hub and the introducer hub so as to inhibit both axial and rotational disengagement of the dilator hub and the introducer hub; the means for releasably locking the dilator hub and the introducer hub further comprising:
  (1) two grooves, each of the grooves having a first portion generally axially aligned with the longitudinal axis, and a second portion generally circumferentially aligned with the longitudinal axis;
  (2) two protrusions, each complementarily engaging one of the grooves; and,
  (3) a tapered male member associated with the dilator hub and a tapered female member associated with the introducer hub.

* * * * *